US 11,452,489 B2

(12) United States Patent
Sorger et al.

(10) Patent No.: US 11,452,489 B2
(45) Date of Patent: Sep. 27, 2022

(54) RADIATION FINDER TOOL

(71) Applicant: Intuitive Surgical Operations, Inc., Sunnyvale, CA (US)

(72) Inventors: Jonathan M. Sorger, Belmont, CA (US); Ian E. McDowall, Woodside, CA (US); Theodore W. Rogers, Alameda, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 95 days.

(21) Appl. No.: 16/652,509

(22) PCT Filed: Oct. 1, 2018

(86) PCT No.: PCT/US2018/053828
§ 371 (c)(1),
(2) Date: Mar. 31, 2020

(87) PCT Pub. No.: WO2019/070616
PCT Pub. Date: Apr. 11, 2019

(65) Prior Publication Data
US 2020/0268329 A1   Aug. 27, 2020

Related U.S. Application Data

(60) Provisional application No. 62/566,693, filed on Oct. 2, 2017.

(51) Int. Cl.
*A61B 6/06*    (2006.01)
*A61B 6/12*    (2006.01)
(Continued)

(52) U.S. Cl.
CPC .............. *A61B 6/4258* (2013.01); *A61B 6/06* (2013.01); *A61B 6/4057* (2013.01);
(Continued)

(58) Field of Classification Search
CPC ....... A61B 6/4057; A61B 6/4258; A61B 6/12; A61B 6/4405; G01T 1/20181; G01T 1/242
See application file for complete search history.

(56) References Cited

U.S. PATENT DOCUMENTS 4,631,409 A * 12/1986 Sparacia ............... G01T 1/2002
250/361 R
4,801,803 A *  1/1989 Denen .................... H03F 3/1935
250/336.1

(Continued)

FOREIGN PATENT DOCUMENTS

WO    WO-9015346 A2 * 12/1990 ........... A61N 5/1014
WO    WO-2005112560 A2 * 12/2005 ........... A61B 6/4258
WO    WO-2012147034 A1    11/2012

OTHER PUBLICATIONS

Koyama et al., "Development of Pixelated Photon Detector Using Silicon on Insulation Technology for TOF-PET" International Workshop on SOI Pixel Detector (SOIPIX2015), Sendai, Japan, Jun. 2015 (Year: 2015).*

(Continued)

*Primary Examiner* — Colin T. Sakamoto (57) ABSTRACT

A radiation finder tool assists in locating tissue of interest within a patient. The radiation finder tool includes a body and a plurality of radiation detectors. The body has a distal end, a proximal end. A lengthwise axis of the radiation finder tool extends between the proximal end and the distal end of the body. The plurality of radiation detectors is oriented serially along the lengthwise axis, e.g., stacked one after the other along the lengthwise axis. Each radiation detector of the plurality of radiation detectors has a different field of view for radiation detected by that radiation detector. Each field of view of the plurality of radiation detectors has the lengthwise axis at its center.

20 Claims, 7 Drawing Sheets

(51) Int. Cl.
*G01T 1/20* (2006.01)
*A61B 6/00* (2006.01)
*A61B 8/00* (2006.01)

(52) U.S. Cl.
CPC .......... *A61B 6/4266* (2013.01); *A61B 6/4405* (2013.01); *A61B 6/4417* (2013.01); *A61B 6/46* (2013.01); *A61B 8/4416* (2013.01); *G01T 1/20181* (2020.05)

(56) References Cited

U.S. PATENT DOCUMENTS

| | | | | |
|---|---|---|---|---|
| 4,889,991 | A * | 12/1989 | Ramsey | A61B 6/4258 250/363.01 |
| 4,893,013 | A * | 1/1990 | Denen | G01T 1/161 250/336.1 |
| 4,959,547 | A * | 9/1990 | Carroll | G01T 1/161 250/336.1 |
| 5,008,546 | A * | 4/1991 | Mazziotta | G01T 1/169 250/366 |
| 5,036,201 | A * | 7/1991 | Carroll | G01T 1/161 250/336.1 |
| 5,070,878 | A * | 12/1991 | Denen | A61B 6/4258 250/336.1 |
| 5,119,818 | A * | 6/1992 | Carroll | A61B 10/0233 250/336.1 |
| 5,151,598 | A * | 9/1992 | Denen | H03F 3/1935 600/431 |
| 5,170,055 | A * | 12/1992 | Carroll | G01T 1/161 250/336.1 |
| 5,694,933 | A * | 12/1997 | Madden | A61B 6/482 600/431 |
| 5,744,805 | A * | 4/1998 | Raylman | A61B 6/425 250/370.06 |
| 5,857,463 | A * | 1/1999 | Thurston | G01T 1/161 600/431 |
| 5,932,879 | A * | 8/1999 | Raylman | A61B 6/425 250/370.06 |
| 6,076,009 | A * | 6/2000 | Raylman | A61B 6/425 250/303 |
| 6,191,422 | B1 * | 2/2001 | Thurston | A61B 6/4258 250/367 |
| 6,204,505 | B1 * | 3/2001 | Call | A61B 6/4258 250/370.01 |
| 6,218,669 | B1 * | 4/2001 | Call | A61B 6/4258 250/336.1 |
| 6,236,880 | B1 * | 5/2001 | Raylman | G01T 1/161 600/436 |
| 6,242,741 | B1 * | 6/2001 | Miller | A61B 6/548 250/363.02 |
| 6,331,703 | B1 * | 12/2001 | Yarnall | A61B 6/4057 250/336.1 |
| 6,416,462 | B1 * | 7/2002 | Tovey | A61B 6/4423 600/125 |
| 6,643,538 | B1 | 11/2003 | Majewski et al. | |
| 6,771,802 | B1 * | 8/2004 | Patt | A61B 6/4258 382/128 |
| 9,784,852 | B1 * | 10/2017 | Majewski | G01T 1/161 |
| 2002/0063204 | A1 * | 5/2002 | Yarnall | G01T 1/161 250/252.1 |
| 2002/0188197 | A1 * | 12/2002 | Bishop | A61B 5/02755 600/431 |
| 2003/0004407 | A1 * | 1/2003 | Carroll | G01T 1/161 600/407 |
| 2004/0054248 | A1 * | 3/2004 | Kimchy | A61B 6/4057 600/3 |
| 2006/0049351 | A1 * | 3/2006 | Bushberg | G01T 1/161 250/336.1 |
| 2008/0272308 | A1 * | 11/2008 | Samson, Jr. | G01T 1/242 250/336.1 |
| 2009/0030310 | A1 * | 1/2009 | Hamill | G01T 1/161 600/407 |
| 2009/0309032 | A1 | 12/2009 | Ramsden et al. | |
| 2010/0010343 | A1 * | 1/2010 | Daghighian | A61B 6/4233 250/370.11 |
| 2010/0010346 | A1 | 1/2010 | Greenleaf et al. | |
| 2011/0121192 | A1 | 5/2011 | Moriya et al. | |
| 2011/0233421 | A1 * | 9/2011 | Thurston | G01T 1/161 250/393 |
| 2011/0260072 | A1 * | 10/2011 | Guerin | G01T 1/242 382/128 |
| 2014/0051904 | A1 * | 2/2014 | Solf | G01V 5/0041 600/3 |
| 2014/0309529 | A1 * | 10/2014 | O'Neill | A61B 6/4258 600/436 |
| 2016/0135762 | A1 * | 5/2016 | Mihailescu | A61B 6/547 600/424 |
| 2016/0170035 | A1 * | 6/2016 | Yarnall | A61B 6/12 600/436 |
| 2016/0306052 | A1 | 10/2016 | Ramsden et al. | |
| 2017/0079609 | A1 * | 3/2017 | Pani | A61B 8/463 |
| 2018/0177481 | A1 * | 6/2018 | Jacob | A61B 6/032 |
| 2018/0235556 | A1 * | 8/2018 | Speeg | A61B 6/4423 |
| 2018/0303445 | A1 * | 10/2018 | Subramanian | A61B 6/425 |
| 2018/0328863 | A1 * | 11/2018 | Rui | G01T 1/242 |
| 2020/0057168 | A1 * | 2/2020 | Evrard | G01T 1/2006 |
| 2020/0196964 | A1 * | 6/2020 | Speeg | G01T 1/244 |

OTHER PUBLICATIONS

Pourtangestani et al., "Optimization of plastic scintillator thicknesses for online beta/gamma detection" EPJ Web of Conferences 24, 07010, 2012 (Year: 2012).*

Peng et al., "Recent Developments in PET Instrumentation" Current Pharmaceutical Biotechnology 2010, 11(6), author manuscript published 2013 (Year: 2013).*

Zanzonico et al., "The Intraoperative Gamma Probe: Basic Principles and Choices Available" Seminars in Nuclear Medicine, vol. XXX, No. 1 (Jan.), 2000: pp. 33-48 (Year: 2000).*

Heller et al., "Nuclear Probes and Intraoperative Gamma Cameras" j.semnuclmed.2010.12.004 (Year: 2010).*

Raylman, "Performance of a Dual, Solid-State Intraoperative Probe System with 18F, 99mTc, and 111In" The Journal of Nuclear Medicine, vol. 42, No. 2, Feb. 2001 (Year: 2001).*

Watanabe et al., "CdTe stacked detectors for Gamma-ray detection" 2001 IEEE Nuclear Science Symposium Conference Record (Cat. No. 01CH37310), 2001, pp. 2434-2438 vol. 4 (Year: 2001).*

International Preliminary Report on Patentability for Application No. PCT/US2018/053828, dated Apr. 16, 2020, 6 pages.

International Search Report and Written Opinion for Application No. PCT/US2018/053828, dated Apr. 9, 2019, 9 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP18864516.2 dated May 26, 2021, 13 pages.

* cited by examiner

RADIATION FINDER TOOL

RELATED APPLICATIONS

The present application claims priority to U.S. Provisional Patent Application No. 62/566,693, filed on Oct. 2, 2017, and entitled "Radiation Finder Tool," the contents of which are hereby incorporated by reference in their entirety.

BACKGROUND OF THE INVENTION

Field of the Invention

The present invention relates generally to surgical instruments, and more particularly to imaging instruments.

Description of Related Art

Figure 1:
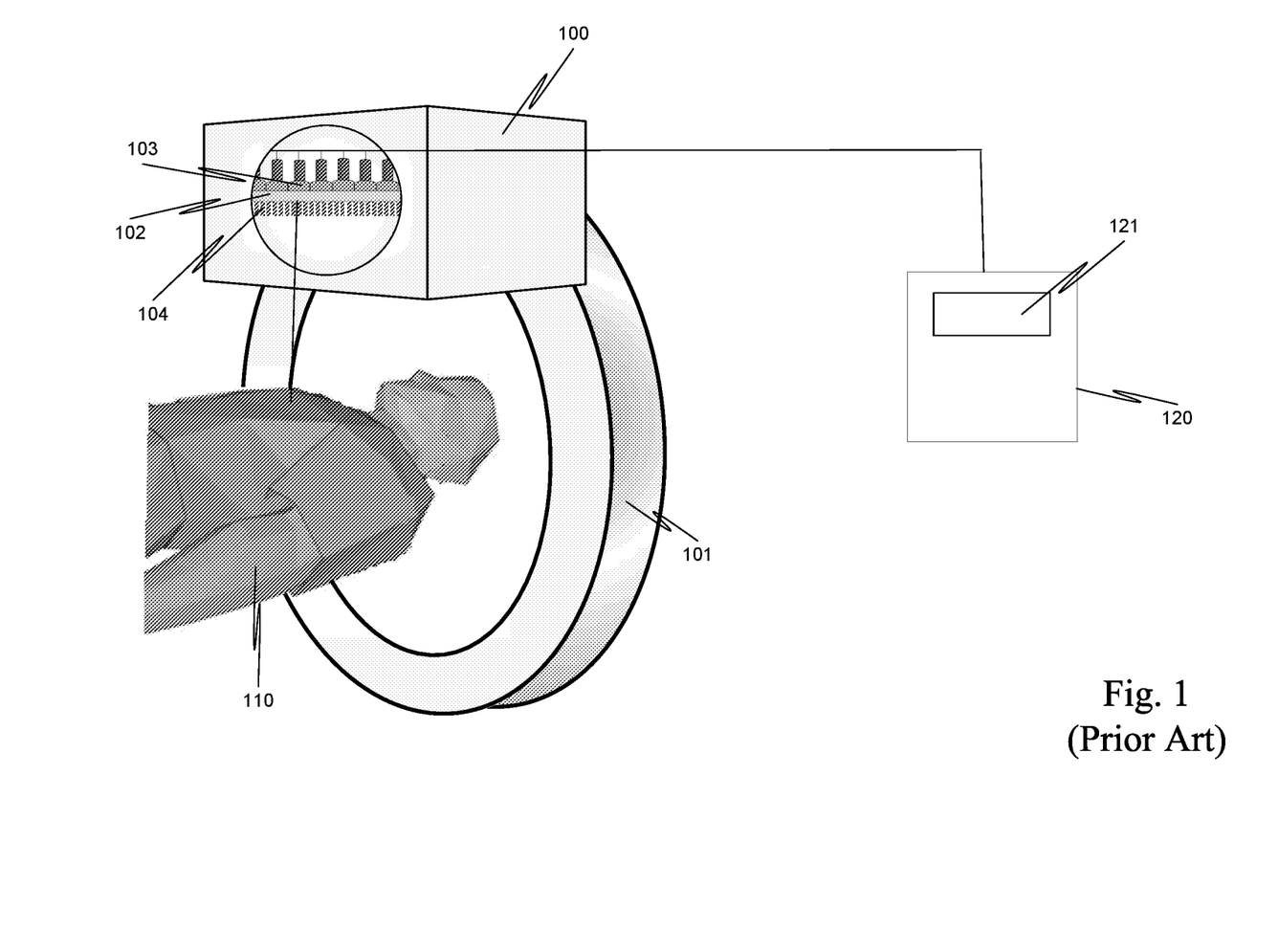
FIG. 1 is an example of one prior art gamma camera 100.

Gamma cameras are known and used in the medical industry. FIG. 1 is an example of one prior art gamma camera 100. Gamma camera 100 is mounted on a circular carriage 101 so that gamma camera 100 can move around patient 110.

Patient 110 is injected with a tracer that emits gamma rays. A common tracer is Technetium. At least some of the gamma rays from the tracer injected into patient 110, which are incident on gamma camera 100, are converted into an electrical signal that is provided to a processing system 120. Processing system 120 converts the electrical signals from gamma camera 100 into an image of patient 110, which is displayed on monitor 121 of processing system 120. Unlike X-ray imaging that produces an anatomical image, gamma camera 100 produces a functional image, e.g., an image of locations that preferentially absorb the injected tracer.

Gamma camera 100 includes a collimator 104, which is typically made of lead, a crystal 102, and a bank of photomultiplier tubes 103. Collimator 104 passes gamma rays that are aligned with openings in collimator 104 to crystal 102. Crystal 102, such as a sodium iodide crystal, converts the gamma rays to photons of light. The photons of light from crystal 102 are picked up by the bank of photomultiplier tubes 103 and converted to an electrical output that is supplied to processing system 120.

Figure 2A:
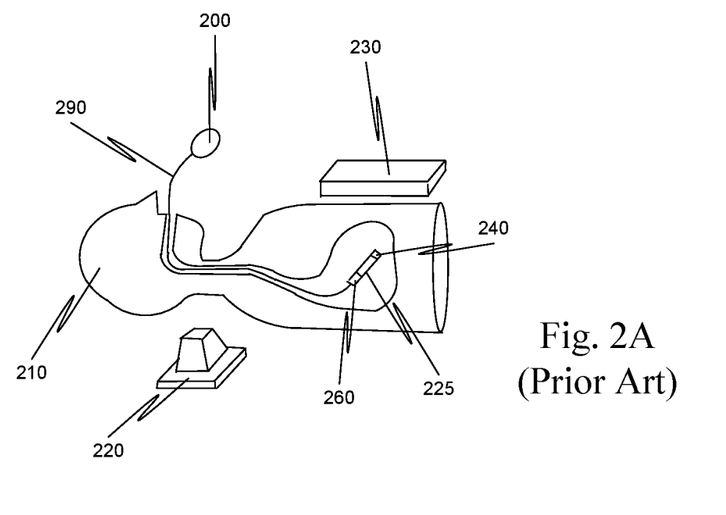
FIGS. 2A and 2B illustrate another prior art gamma probe and gamma camera.
Figure 2B:
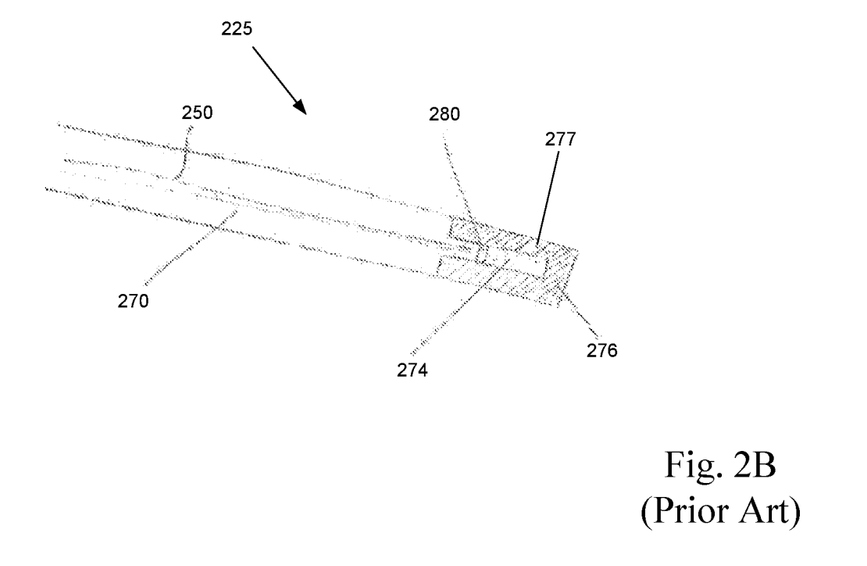

FIGS. 2A and 2B illustrate another use of a gamma probe 225 and a gamma camera 230, as disclosed in U.S. Pat. No. 9,345,441 B2. In FIG. 2A, gamma probe 225 is located completely in the patient 210 and is moved/orientated from outside patient 210 using mechanical or electric control 200 of a gastroscope 290. Gamma probe 225 is an elongated body at one end of gastroscope 290. Gastroscope 290 is inserted into the stomach of patient 210 through the esophagus. In one aspect, gamma probe 225 also includes an electromagnetic sensor 240 for the tracking, and an ultrasonic transmitter and probe 260 that generate additional image information.

An electromagnetic tracking system 220 monitors the location of gamma probe 225. Gamma camera 230, which is positioned above and outside patient 210, operates in coincidence with gamma probe 225. Gamma camera 230 supplies further information for imaging. In this case, gamma probe 225 (the elongated body at the end of the gastroscope 290) and the gamma camera 230 are tracked by tracking system 220.

FIG. 2B is a more detailed illustration of a typical laproscope that includes gamma probe 225. Gamma probe 225 includes a housing 270, at one end of which is attached a tungsten collimator 276. Collimator 276 has a laterally directed opening 277, which determines the detection characteristic through a field of view. Laterally directed opening 277 is a window in tungsten collimator 276 with an opening angle of approximately 70 degrees.

A scintillator crystal 274 is located in tungsten collimator 276. A silicon photomultiplier 280 in addition to scintillator crystal 274 is located in collimator 426. Silicon photomultiplier 280 converts the incident light generated by scintillator crystal 274 into an electrical signal on a cable 250. Silicon photomultiplier 280 is connected to the outside world via cable 250.

SUMMARY

A novel radiation finder tool assists in locating tissue of interest within a patient. In one aspect, the radiation finder tool includes a body and a plurality of radiation detectors. The body has a distal end and a proximal end. A lengthwise axis of the radiation finder tool extends between the proximal end and the distal end of the body. The plurality of radiation detectors is oriented serially along the lengthwise axis, e.g., stacked one after the other along the lengthwise axis so that the lengthwise axis of each of the plurality of radiation detectors extends in the same direction as the lengthwise axis of the radiation finder tool. Each radiation detector of the plurality of radiation detectors has a different field of view for radiation detected by that radiation detector. Each field of view of the plurality of radiation detectors has the lengthwise axis of the radiation finder tool at its center.

In one aspect, the body of the radiation finder tool has an outer surface. In this aspect, the radiation finder tool includes one or more visual radiation detection indicators mounted on the outer surface of the body. Each of the one or more visual radiation detection indicators is coupled to a different one of the plurality of radiation detectors so that when a radiation detector senses radiation, the state of the corresponding visual radiation detection indicator changes. In one aspect, each of the one or more visual radiation detection indicators is a different visual indicator ring surrounding the outer surface of the body.

In one aspect of the radiation finder tool, each of the plurality of radiation detectors includes a scintillator configured to receive radiation incident on the radiation detector, and a photon detector coupled to the scintillator. In one aspect, the photon detector is a solid state device that changes light photons from the scintillator into an electrical signal such as an array of Geiger-mode avalanche photo diodes. In one aspect, the photon detector is a solid-state single photon avalanche diode (SPAD) detector array coupled to the scintillator.

In yet a further aspect, the scintillator of one or more of the plurality of radiation detectors has a mirrored surface configured to reflect photons back to the photon detector. In other aspects, the radiation finder tool includes an image capture unit, or alternatively an ultrasound unit.

In another aspect, a radiation finder tool includes a body, a first collimator, a first radiation detector, a second collimator, and a second radiation detector. The first collimator is mounted in the body. The first collimator has a proximal end and a distal end. The first radiation detector is mounted in the first collimator.

The second collimator is also mounted in the body. The second collimator has a proximal end and a distal end. The distal end of the second collimator is proximal to the proximal end of the first collimator. The second radiation detector is mounted in the second collimator. The second radiation detector is configured to receive radiation passed through the first radiation detector.

In this aspect, the body of the radiation finder tool has an outer surface, and the radiation finder tool further includes a first visual radiation detection indicator mounted on the outer surface of the body and coupled to the first radiation detector, and a second visual radiation detection indicator mounted on the outer surface of the body and coupled to the second radiation detector. In one aspect, each of the first and second visual radiation detection indicators is a different visual indicator ring surrounding the outer surface of the body.

The first radiation detector of the radiation finder tool includes a first scintillator configured to receive radiation incident on the first radiation detector and a first photon detector coupled to the first scintillator. The second radiation detector includes a second scintillator configured to receive radiation incident on the second radiation detector and a second photon detector coupled to the second scintillator. Each of the first and second photon detectors is a solid-state photon detector array, such as a solid-state single photon avalanche diode detector array.

A diagnostic method for locating tissue of interest in a patient includes positioning a radiation finder tool over tissue of a patient. The radiation finder tool includes a plurality of radiation detectors stacked along a lengthwise axis of the radiation finder tool so that a lengthwise axis of each of the plurality of radiation detectors is coincident with the lengthwise axis of the radiation finder tool. The lengthwise axis of the radiation finder tool extends between a distal end and a proximal end of the radiation finder tool. The diagnostic method also includes determining a number of the plurality of radiation detectors sensing radiation. If less than all of the plurality of radiation detectors sense radiation, the positioning and determining processes are repeated. Conversely, if all of the plurality of radiation detectors sense radiation, the method is stopped, because the distal end of the radiation finder tool points at a location of the tissue of interest.

BRIEF DESCRIPTION OF THE DRAWINGS

In the drawings, the first digit in the reference numeral of an element is the number of the figure in which that element first appears.

DETAILED DESCRIPTION

A radiation finder tool 320 (FIG. 3A) assists a surgeon in locating a site 301 emitting radiation within a patient 300. A radiation source is introduced into patient 300. The radiation source, e.g., the common tracer Technetium, is configured to or does preferentially accumulate in tissue of interest.

Figure 3A:
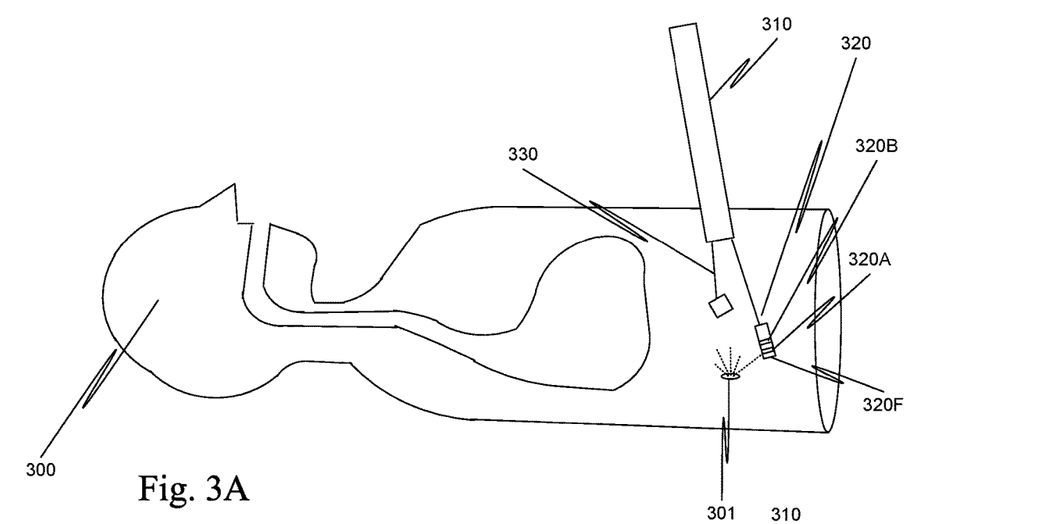
FIGS. 3A to 3D illustrate a radiation finder tool used to find a site emitting radiation.

When radiation finder tool 320 is positioned over or near tissue of interest 301, which is emitting radiation from the accumulated radiation source, radiation finder tool 320 indicates that tissue of interest 301, sometimes referred to as site 301, is within the field of view of one or more stacked radiation detectors of radiation finder tool 320.

Specifically, a plurality of radiation detectors is oriented serially along a lengthwise axis of radiation finder tool 320, e.g., stacked along the lengthwise axis, so that radiation traveling along the lengthwise axis can pass through each of the plurality of radiation detectors if the radiation has sufficient energy, and so that the centerlines of the fields of view of the plurality of radiation detectors are oriented in the same direction as the lengthwise axis of radiation finder tool 320. If the radiation is traveling at too great an angle to the lengthwise axis, the radiation may pass through none of the plurality of radiation detectors or may pass through less than all of the radiation detectors. A user of radiation finder tool 320 is provided an indication, visual or audio, of the number of radiation detectors that sensed radiation.

By moving radiation finder tool 320, as described more completely below, so that all of the plurality radiation detectors sense radiation, the site that is emitting the radiation can be identified because the radiation from the site is within the field of view of all the stacked radiation detectors of radiation finder tool 320. Thus, the distal end of radiation finder tool 320 points at (is aligned with) site 301, when all of the plurality radiation detectors sense radiation. As used herein, radiation refers to electromagnetic radiation having a wavelength shorter than the wavelengths in the ultraviolet spectrum.

As mentioned above, radiation finder tool 320 includes a plurality of radiation detectors stacked along a lengthwise axis, sometimes referred to as a longitudinal axis, of radiation finder tool 320. There is shielding around the plurality of radiation detectors so that only radiation within a detection zone around the lengthwise axis of radiation finder tool 320 can activate each of the plurality of radiation detectors.

In the example of FIG. 3A, a plurality of instruments, e.g., a camera instrument 330 and radiation finder tool 320 are introduced into patient 300 using a common guide tube 310. While it is not shown in FIGS. 3A to 3C, the plurality of instruments and common guide tube 310, in one aspect, are coupled to a cart which is part of a computer-assisted teleoperated system.

In the computer-assisted teleoperated system, the cart is coupled to a control system and to a surgeon's system interface. The surgeon's system interface includes a display device and one or more master tool grips. The master tool grips (masters) are used by a surgeon to control the plurality of teleoperated instruments (slaves). Examples of computer-assisted teleoperated systems that include a plurality of teleoperated instruments are presented, for example, in U.S. Patent Application Publication No. 2008-0065105 A1 (filed Jun. 13, 2007; disclosing Minimally Invasive Surgical System) and U.S. Pat. No. 6,331,181 (filed Dec. 18, 2001; disclosing Surgical Robotic Tools, Data Architecture, and Use), each of which is incorporated herein by reference.

The example of a computer-assisted teleoperated system is illustrative only and is not intended to be limiting. Radiation finder tool 320 could also be used in a manually operated endoscope or a computer-assisted endoscope through which one or more tools are extended. See for example, U.S. Patent Application Publication 2005/0090709 A1 for an example of a manually operated endoscope in which radiation finder tool 320 could be incorporated. Alternatively, radiation finder tool 320 could be used at the distal end of a laproscope.

In this example, radiation finder tool 320 includes a visual radiation detection indicator, sometimes referred to as visual indicator, on an outer surface of radiation finder tool 320. The visual indicator provides a visual output that is indicative of the number of radiation detectors in the plurality of radiation detectors that are measuring radiation.

In FIG. 3A, radiation finder tool 320 is oriented such that none of the radiation from site 301 can enter distal face 320F of radiation finder tool 320. Thus, the visual indicator, which in this example is a plurality of visual indicator bands 320A, 320B on the outer surface of radiation finder tool 320, provides no visual output, because none of the radiation detectors in the plurality of radiation detectors is measuring, sometimes referred to as sensing, radiation.

Figure 3B:
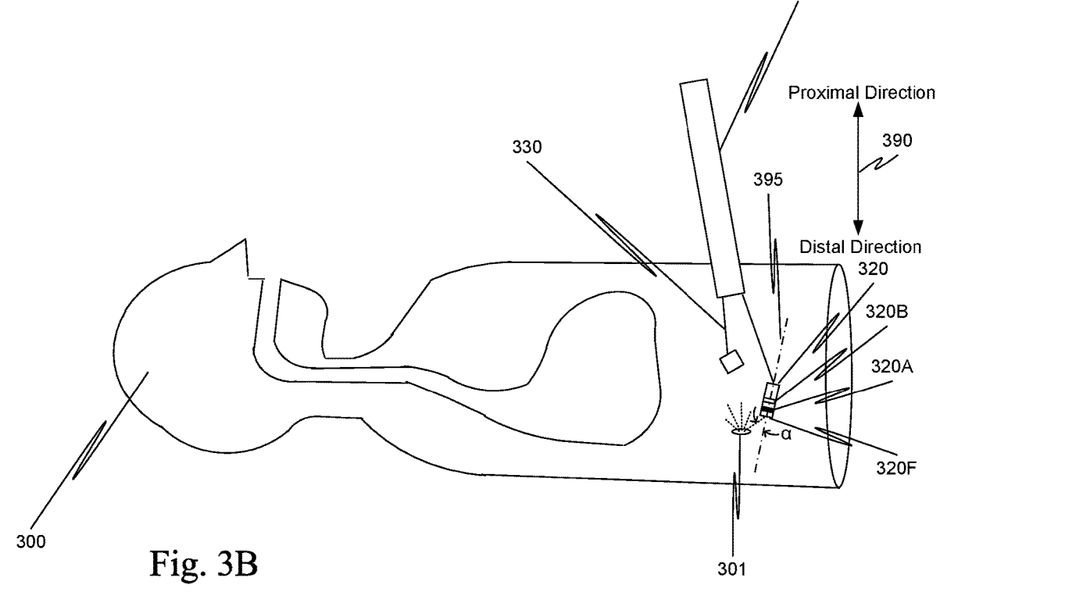

In FIG. 3B, the orientation of radiation finder tool 320 is changed, and some of the radiation from site 301 enters distal face 320F of radiation finder tool 320. However, angle α between the radiation that enters distal face 320F and lengthwise axis 395 of radiation finder tool 320 is large enough that the radiation only interacts with the most distal radiation detector in the plurality of radiation detectors. (In FIGS. 3A and 3B, arrow 390 defines the distal direction (a first direction) and the proximal direction (a second direction)). Thus, in the visual indicator, most distal visual indicator band 320A changes color to indicate that the most distal radiation detector has sensed radiation.

The change in color of most distal visual indicator band 320A is captured by camera instrument 330 and is displayed in an image of the site that is presented to the surgeon. Typically, the site is internal to the patient. Thus, the surgeon upon viewing the color change of most distal visual indicator band 320A of radiation finder tool 320 in the image of the site knows the radiation finder tool 320 is in the vicinity of site 301, but is not yet pointing directly at site 301.

Figure 3C:
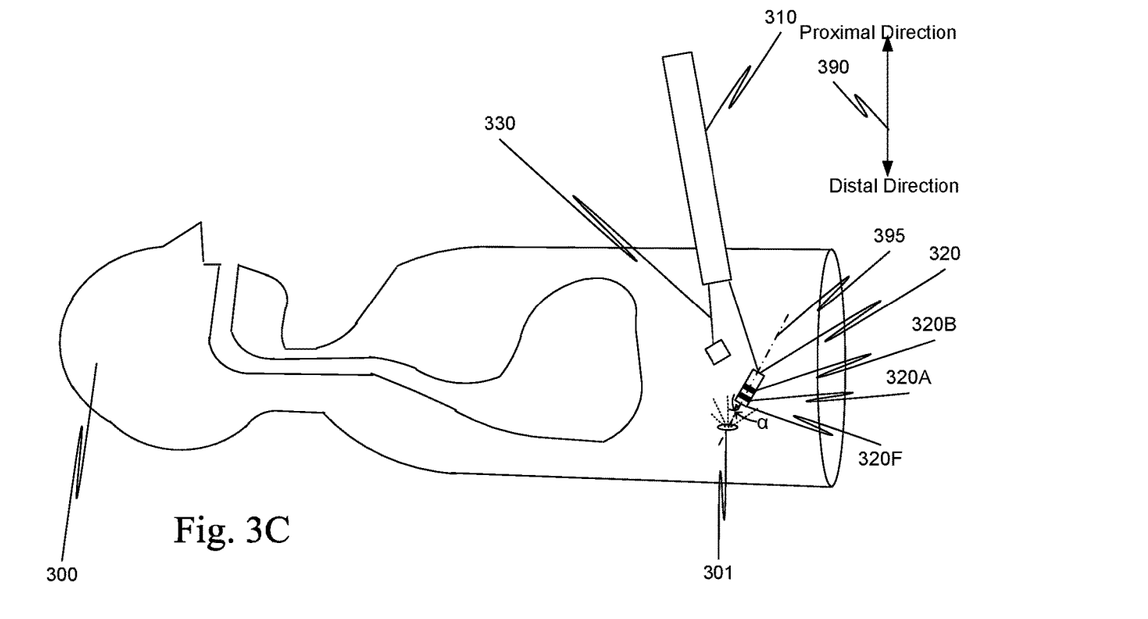

In FIG. 3C, the orientation of radiation finder tool 320 is changed still further so that angle α between radiation that enters distal face 320F and lengthwise axis 395 of radiation finder tool 320 is nearly zero degrees. Thus, the radiation that enters distal face 320F interacts with each of the radiation detectors in the plurality of radiation detectors.

Thus, in addition to most distal visual indicator band 320A, visual indicator, indicator band 320B changes color, and so visual indicator bands 320A and 320B indicate that the radiation emitted from site 301 has interacted with each of the plurality of radiation detectors. Both of visual indicator bands 320A, 320B have changed color and the color of visual indicator bands 320A and 320B is captured by camera instrument 330 and is displayed in the image presented to the surgeon. Thus, the surgeon upon viewing the color of visual indicator bands 320A, 320B of radiation finder tool 320 in the image of the site knows that the radiation finder tool 320 is pointing directly at site 301.

The use of a visual indicator on radiation finder tool 320 to show when the extended lengthwise axis 395, sometimes referred to as longitudinal axis 395, of radiation finder tool 320 extends though site 301 is illustrative only and is not intended to be limiting. In another aspect, the visual indicator is not on radiation finder tool 320 itself, but rather signals from the plurality radiation detectors in radiation finder tool 320 are coupled to a controller that in turn controls a radiation finder tool interface in a display viewed by the surgeon. The radiation finder tool interface could be, for example, a bar in the display that changes as radiation finder tool 320 becomes better aligned with the source of radiation. Alternatively, the controller could generate an audio sound that changes to indicate optimal alignment, where extended longitudinal axis 395 of radiation finder tool 320 intersects site 301. In one aspect, the audio feedback is combined with a visual indicator.

In some instances the tissue of interest may not be localized at a particular site as illustrated in FIGS. 3A to 3C. Rather, the tissue of interest that includes the radiation source may be distributed in an area of the displayed site, e.g., a nerve, a lumen, or a particular type of tissue. In this case, the operator uses radiation finder tool 320 to manually scan the site to determine the extent of the anatomical feature emitting the radiation. The manual scan can be done by the surgeon using a teleoperated master grip or other master grip used to control a slave radiation finder tool, such as radiation finder tool 320.

Figure 3D:
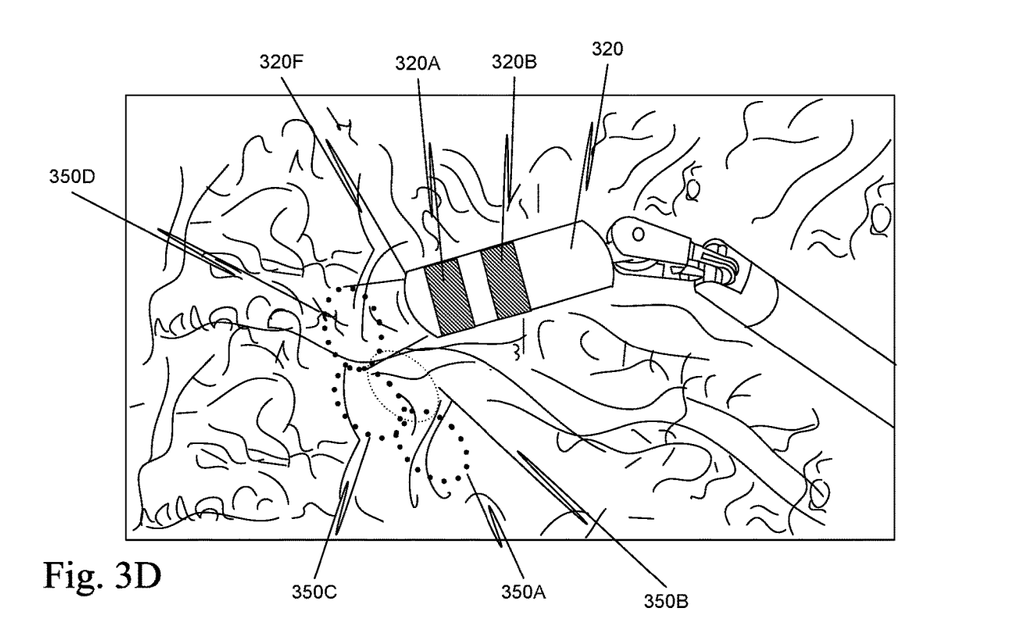

FIG. 3D is a representation of a displayed image of a site of interest that is internal to a patient. This image includes an image of a teleoperated radiation finder tool 320. Radiation finder tool 320 is being used to scan the site of interest. In this example, when one or all of visual indicator bands 320A, 320B have changed color, i.e., when any or all of the plurality of radiation detectors sense radiation, a controller draws an outline of the perimeter of the field of view of radiation finder tool 320 on the site, e.g., outlines 350A, 350B, 350C and 350D, in the displayed image. Since the anatomical feature emitting the radiation may be below the surface of the tissue viewed by the surgeon, outlines 350A, 350B, 350C and 350D help the surgeon visual the location of the anatomical feature of interest. Even when the anatomical feature of interest is not below the surface, outlines 350A, 350B, 350C and 350D help the surgeon determine the extent of the anatomical feature of interest.

In some aspects, the outline of the field of view represents the outline of the field of view of the radiation detector with the smallest field of view that sensed radiation. In another aspect, the type of line—solid, dashed, dotted, green, blue, etc.—that is used to outline the field of view denotes the number of radiation detectors that sensed radiation, while the field of view outline is the outline of the field of view of the most distal radiation detector. Various combinations of these aspects can be combined to present a representation of the fields of view at the various locations, and so these examples are not intended to be limiting.

Figure 4A:
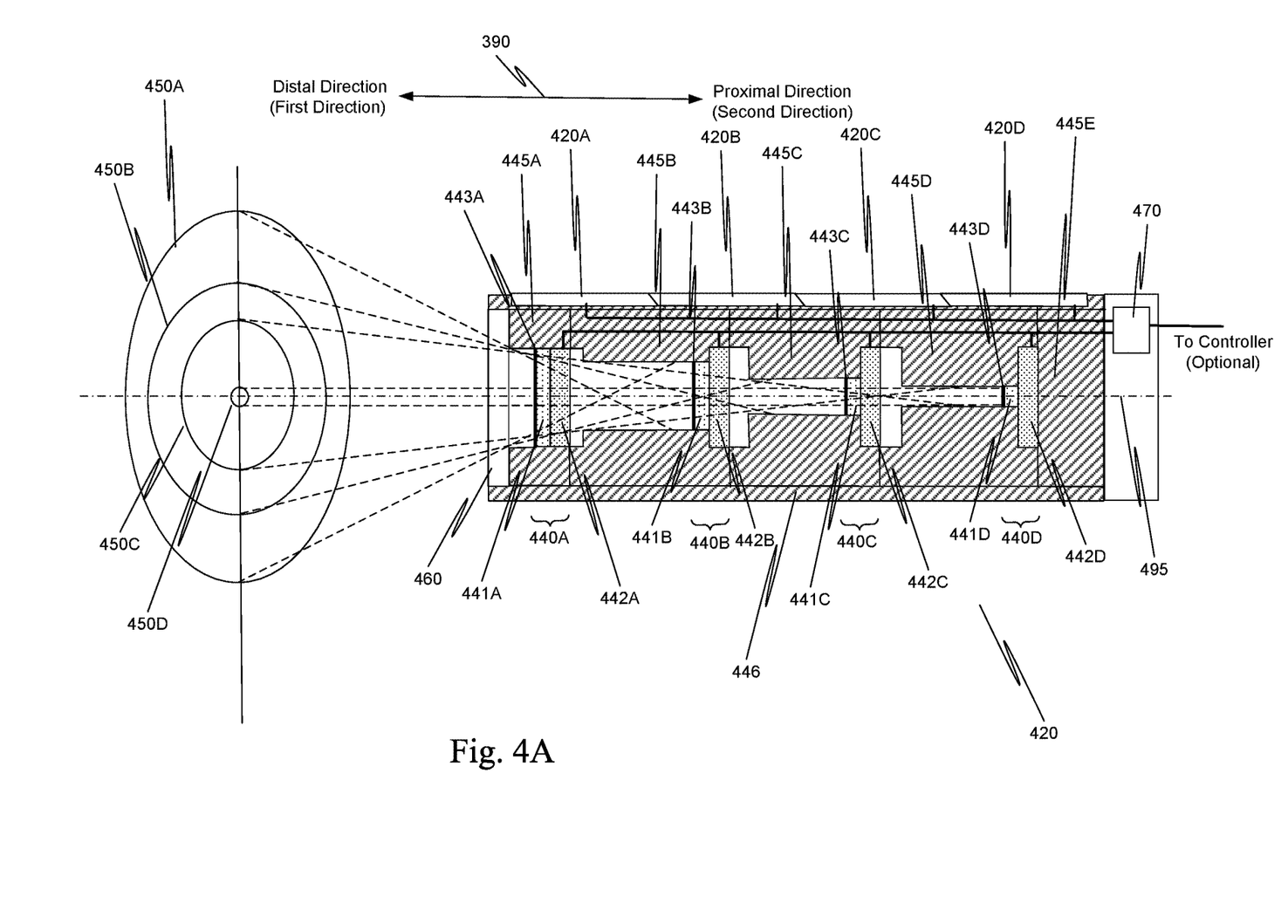
FIG. 4A is a cut-away view of one aspect of a radiation finder tool.

FIG. 4 is a cut-away view of one example of radiation finder tool 320. Radiation finder tool 420 includes a plurality of radiation detectors 440A, 440B, 440C, and 440D. The use of four radiation detectors is illustration only, and is not intended to be limiting. Radiation finder tool 320 includes at least two radiation detectors, but can include more. Plurality of radiation detectors 440A, 440B, 440C, and 440D is oriented serially along lengthwise axis 495, e.g., stacked along lengthwise axis 495 one after another so that radiation exiting from a more distal radiation detector passes into an adjacent proximal radiation detector. In this example, the lengthwise axis of each of plurality of radiation detectors 440A, 440B, 440C, and 440D is coincident with lengthwise axis 495 of radiation finder tool 320. Similarly, the centerline of each of the fields of view of plurality of radiation detectors 440A, 440B, 440C, and 440D extends in a same direction as lengthwise axis 495 of radiation finder tool 320.

Each radiation detector of plurality of radiation detectors 440A, 440B, 440C, and 440D includes a scintillator and a photon counter. For example, radiation detector 440A includes scintillator 441A and photon counter 442A; radiation detector 440B includes scintillator 441B and photon counter 442B; radiation detector 440C includes scintillator 441C and photon counter 442C; and radiation detector 440D includes scintillator 441D and photon counter 442D.

Each of plurality of radiation detectors 440A, 440B, 440C, and 440D has a different field of view, which, in this aspect, is determined in part by a distance of the radiation detector from a window 460 in the distal end of radiation finder tool 420. The distance is measured along lengthwise axis 495 that extends between the distal and proximal ends of radiation finder tool 420.

Radiation detector 440A is closest to window 460 and has a largest area in a plane substantially parallel to window 460 and substantially perpendicular to lengthwise axis 495. Radiation detector 440B is second closest to window 460 and has an area in the plane substantially parallel to window 460 and substantially perpendicular to lengthwise axis 495 that is smaller than the corresponding area of radiation detector 440A in that plane. Radiation detector 440C is third closest to window 460 and has an area in the plane substantially parallel to window 460 and substantially perpendicular to lengthwise axis 495 that is smaller than the corresponding area of radiation detector 440B in that plane. Radiation detector 440D is farthest from window 460 and has an area in the plane substantially parallel to window 460 and substantially perpendicular to lengthwise axis 495 that is smaller than the corresponding area of radiation detector 440C in that plane. Here, substantially parallel and substantially perpendicular mean that from a human perspective the plane and the window appear parallel and that from the human perspective, the plane and the axis appear perpendicular.

The area in a plane substantially parallel to window 460 and substantially perpendicular to lengthwise axis 495 of each detector is defined by a collimator for that detector. Collimator 445A for radiation detector 440A has the largest opening about lengthwise axis 495; collimator 445B for radiation detector 440B has a smaller opening about lengthwise axis 495 than collimator 445A; collimator 445C for radiation detector 440C has a smaller opening about lengthwise axis 495 than collimator 445B; collimator 445D for radiation detector 440D has the smallest opening about lengthwise axis 495. In one aspect, each of the collimators is a lead ring, and the proximal end of radiation finder tool 420 includes a lead plug 445E adjacent the proximal end of radiation detector 440D.

The collimators, radiations detectors, and lead plug are mounted within a body 446, in this example. The length of each of the radiation detectors is constrained by the geometry of the radiation finder tool and the total outer diameter of the instrument, which in one aspect is 12 mm, as well as by depth resolution of the radiation finder tool. The materials chosen also affect the design of the radiation detectors.

In the aspect of FIG. 4A, a first radiation detector, e.g., detector 440A, is mounted in a proximal end of a first collimator 445A. A second detector, e.g., any one of radiation detectors 440B, 440C, 440D, is mounted in a proximal end of a second collimator. The distal end of the second collimator is proximal to the proximal end of the first collimator.

On the outer surface of body 446 of radiation finder tool 420 is an optional plurality of visual radiation detection indicators—a different one for each of plurality of radiation detectors 440A, 440B, 440C, and 440D, e.g., visual radiation detection indicator 420A for radiation detector 440A, visual radiation detection indicator 420B for radiation detector 440B, visual radiation detection indicator 420C for radiation detector 440C, and visual radiation detection indicator 420D for radiation detector 440D. A visual radiation detection indicator is sometimes referred to as a visual indicator. When a radiation detector measures radiation, the corresponding visual radiation detector indicator is illuminated.

In one aspect, each of plurality of visual radiation detection indicators 420A, 420B, 420C, and 420D includes a light emitting diode (LED), and the color, flash rate, and intensity alone or in any combination can be used to indicate the direction of the radiation as evidenced by detection of radiation. In another aspect, the LED is coupled with a frosted sapphire ring that surrounds body 446 so that the ring lights up around radiation finder tool 420, and so can be seen from any direction. In yet another aspect, the LED is coupled with a frosted sapphire band that surrounds a portion of body 446 so that when the band lights up on radiation finder tool 420, the color change can be seen by a camera instrument, for example.

Each of plurality of visual radiation detection indicators 420A, 420B, 420C, and 420D is coupled to the corresponding radiation detector in plurality of radiation detectors 440A, 440B, 440C, and 440D by an interface circuit 470. In one aspect, interface circuit 470 includes a power source, e.g., a battery, and logic for each radiation detector of plurality of radiation detectors 440A, 440B, 440C, and 440D that receives as an electrical input signal output by that radiation detector and converts the input signal to a signal that drives the corresponding visual radiation detection indicator of plurality of visual radiation detection indicators 420A, 420B, 420C, and 420D.

In another aspect, interface circuit 470 couples visual radiation detection indicators 420A, 420B, 420C and plurality of radiation detectors 440A, 440B, 440C, and 440D to a controller. The controller processes any electrical signals from plurality of radiation detectors 440A, 440B, 440C, and 440D and output signals to corresponding visual radiation detection indicators 420A, 420B, 420C, and 420D to indicate that radiation was detected. Also, the controller can use the information from plurality of radiation detectors 440A, 440B, 440C, and 440D to drive displays presented to the person or persons using or assisting in using radiation finder tool 420 and/or other indicators to indicate the detection of radiation by each of plurality of radiation detectors 440A, 440B, 440C, and 440D, e.g., using a different frequency of sound for each radiation detector. Alternatively, the logic for driving visual radiation detection indicators 420A, 420B, 420C, and 420D could be included in interface circuit 470, described above, but the power is supplied from the controller and the controller also receives the signals from each of the plurality of radiation detectors 440A, 440B, 440C, and 440D.

In one aspect, window 460 is made from any one of a ceramic material, glass, or a metal. The window material selected and the thickness of the selected material is empirically determined so that for radiation energies of interest, all of the plurality of radiation detectors sense radiation for a range of distances between the source of radiation and the distal face of the finder tool typical of those encountered in minimally invasive surgery when the source of radiation is on the extended lengthwise axis of the radiation finder tool.

As indicated previously, each radiation detector of plurality of radiation detectors 440A, 440B, 440C, and 440D includes a scintillator and a photon counter. In one aspect, the scintillator in each radiation detector is a sodium iodide (NaI) polymer, but other known scintillators can also be used. For example, a YAG:Ce (Yttrium Aluminum Garnet activated by Ce3+) poly-ceramic scintillator could be used. See Takayuki Yanagida, et al., *Development of transparent*

*ceramic as scintillators,*" International Workshop on New Photo-detectors PD07, Kobe University, Kobe Japan, (June 2007), which is incorporated herein by reference.

The radiation detectors more distance from window have a smaller field of view, and consequently, the number of gamma rays seen by the more proximal radiation detectors may decrease relative to the more distal radiation detectors. To compensate for the diminished number of gamma rays, in one aspect, the length of the scintillator along lengthwise axis 495 is increased in each of the radiation detectors after the most distal radiation detector based on the distance of the radiation detector from window 460, e.g., based on the distance of the radiation detector from the distal end of radiation finder tool 420 along lengthwise axis 495.

In one aspect, the photon counter in each radiation detector of plurality of radiation detectors 440A, 440B, 440C, and 440D includes solid-state photon detector array that converts light photons to an electrical signal. Typically, the solid-state photon detector array uses avalanche photo diodes. An avalanche photodiode is a high speed, high sensitivity photodiode that multiplies carriers when a high reverse voltage is applied. When an avalanche photodiode is biased just below a breakdown voltage, the avalanche photodiode operates in a linear mode and has a finite multiplication gain. When an avalanche photodiode is biased above a breakdown voltage, the avalanche photodiode has a very large gain and is capable of detecting single photons. Unlike when the avalanche photodiode is operated in the linear range, the signal amplitude from a single photon avalanche diode does not provide intensity information, because the output current pulse has the same amplitude irrespective of whether the pulse is triggered by a single photon or multiple photons. An avalanche photodiode operated so that it can detect single photons is referred to as a Geiger-mode avalanche photo diode. In one aspect, each radiation detector of plurality of radiation detectors 440A, 440B, 440C, and 440D is a solid-state single photon avalanche diode (SPAD) detector array.

The use of a SPAD detector array to detect light photons is known, and so is not considered in further detail. See, for example, Matthew W. Fishburn and Edoardo Charbon, "System Tradeoffs in Gamma-Ray Detection Utilizing SPAD Arrays and Scintillators," *IEEE Transactions on Nuclear Science*, Vol. 57, No. 5, pp. 2549-2557 (October 2010); and D. Renker and E. Lorenz, "Review, Advances in Solid state Photon Detectors," *Jinst*, IOP Publishing for SISSA, 56 pages, (April 2009). See also, "Selection Guide/MPPC and MPRC Module for Precision Measurement," Hamamatsu Phontonics K.K., Solid State Division, Hamamatsu City, Japan, pp. 1 to 23 (March 2016) and "Opto-semiconductor Handbook/Chapter 03 Si APD, MPCC," Hamamatsu Phontonics K.K., Solid State Division, Hamamatsu City, Japan, 25 pgs. (2014).

Figure 4B:
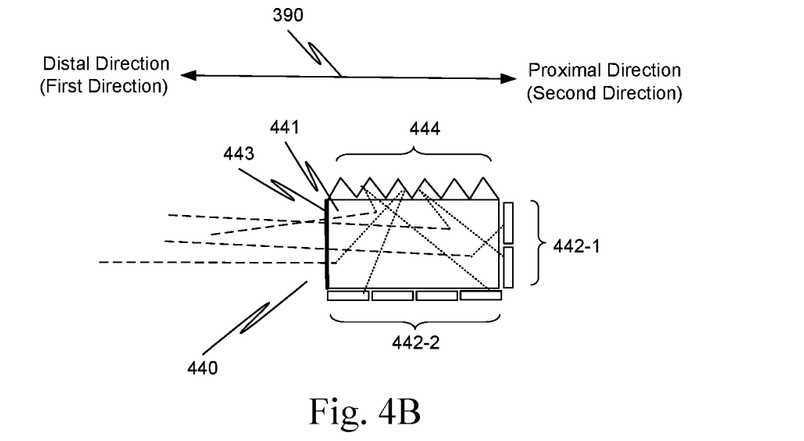
FIG. 4B is an illustration of one aspect of a radiation detector of the radiation finder tool.

In some aspects, optionally, the scintillator in each of the plurality of radiation detectors 440A, 440B, 440C, and 440D is modified to redirect photons heading away from the photon detector back towards the photon detector, and so increase the detection efficiency. In the example of FIG. 4A, each scintillator has a mirrored surface on the distal end surface (a reflective coating on the distal end surface; the distal end surface is sometimes referred to as the distal face) of the scintillator, e.g., mirrored surface 443A on the distal face of scintillator 441A, mirrored surface 443B on the distal face of scintillator 441B, mirrored surface 443C on the distal face of scintillator 441C, and mirrored surface 443D on the distal face of scintillator 441D. The mirrored surface reflects photons that would normally escape through the distal end of the scintillator back toward the photon detector. In some aspect, one or more of the scintillators in each of the plurality of radiation detectors 440A, 440B, 440C, and 440D is modified to redirect photons heading away from the photon detector back towards the photon detector. FIG. 4B is another radiation detector 440 that could be used in radiation finder tool 420 to improve the photon collection efficiency. In this example, a first photon detector 442-1 is placed at the proximal end of scintillator 441 and a second photon detector 442-2 is placed along one side of scintillator 441. On the side of scintillator 441 opposite photon detector 442-2, are corner cube reflectors 444 with the surfaces facing scintillator 441 having a reflective coating. Corner cube reflectors are known and are commercially available. In this aspect, the distal end surface of scintillator 441 also has the optional reflective coating 443.

In FIG. 4B, gamma rays are represented by dashed lines, and photons are represented by dotted lines. FIG. 4B illustrates that photon that would normally escape out of the radiation detector are redirected back to photon detector.

Returning to FIG. 4A, the stack of plurality of radiation detectors 440A, 440B, 440C, and 440D along lengthwise axis 495 causes the fields of view of each of plurality of radiation detectors 440A, 440B, 440C, and 440D to be centered about lengthwise axis 495 with the field of view of radiation detectors 440B, 440C, and 440D decreasing from the field of view of most distal radiation detector 440A. Most distal radiation detector 440A has the largest field of view 450A, while most proximal radiation detector 440D has the smallest field of view 450D. Radiation detector 440B has a field of view 450B that is smaller than field of view 450A or radiation detector 440A and that is larger than field of view 450C of radiation detector 440C. Radiation detector 440C has a field of view 450C that is smaller than field of view 450B or radiation detector 440B and that is larger than field of view 450D of radiation detector 440D.

Figure 5A:
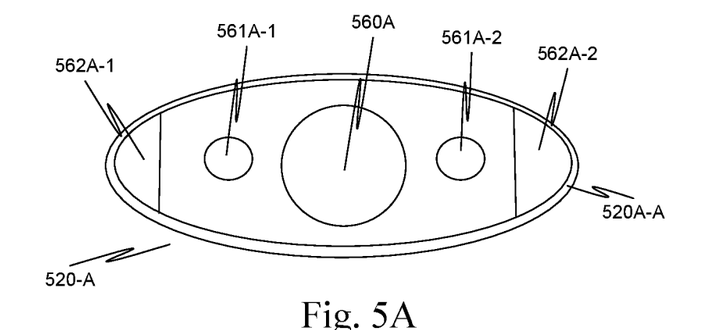
FIGS. 5A and 5B are distal end views of different optional aspects of the radiation finder tool.
Figure 5B:
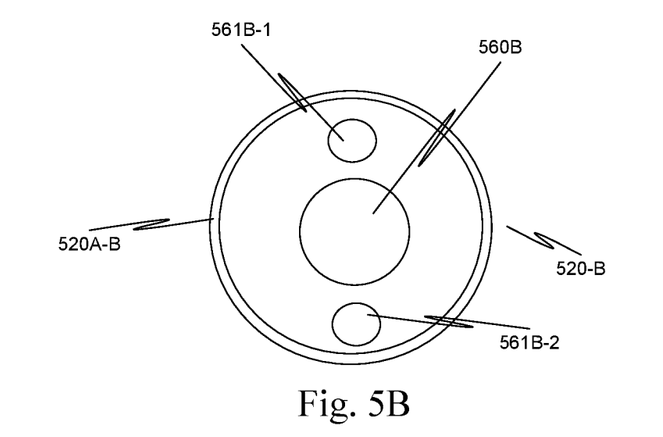

FIGS. 5A and 5B are distal end views of different examples of radiation finder tools. In FIG. 5A, the distal end of radiation finder tool 520-A includes windows 561A-1 and 562A-2 that provide light to stereoscopic cameras, illumination windows 562A-1 and 562A-2 that provide illumination from an illuminator, and window 560A for a plurality of stacked radiation detectors (see FIG. 4A). An illumination ring 520A-A for the first radiation detector in the plurality of stacked radiation detectors is also visible in this view. Radiation finder tool 520-A is advantageous, because a separate instrument to capture an image of the site is not needed. While the visual indicators on the outer surface would not be useful, the radiation detection information from radiation finder tool 520-A can be processed by a controller. The controller can generate a visual indication of the radiation detection status of each of the plurality of radiation detectors in the display viewed by a user.

In FIG. 5B, the distal end of radiation finder tool 520-B includes windows 561B-1 and 562B-2, and window 560B for a plurality of stacked radiation detectors (see FIG. 4A). An illumination ring 520A-B for the first radiation detector in the plurality of stacked radiation detectors is also visible in this view.

In one aspect, window 561B-1 provides light to a monochromatic camera, which, for example, is configured to capture a fluorescence image. In this aspect, window 561B-2 is optional, and could, for example, provide illumination from an illuminator. In another aspect, window 561B-1 provides light to a depth camera. In still another aspect, window 561B-1 passes ultrasound from an ultrasonic generator, and window 561B-2 passes reflected ultrasound to an ultrasound detector. The aspects of radiation finder tool 520-B are advantageous, because radiation finder tool 520-B provides other information, e.g., a fluorescence information or depth information, which is useful in interpreting the radiation detection results.

Figure 6A:
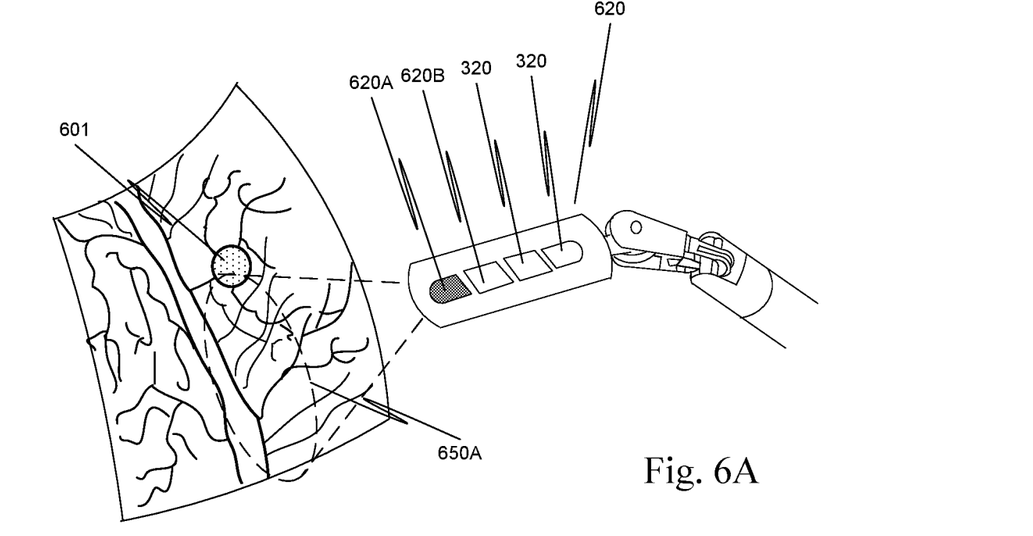
FIGS. 6A to 6B illustrate a radiation finder tool used to find a site emitting radiation.
Figure 6B:
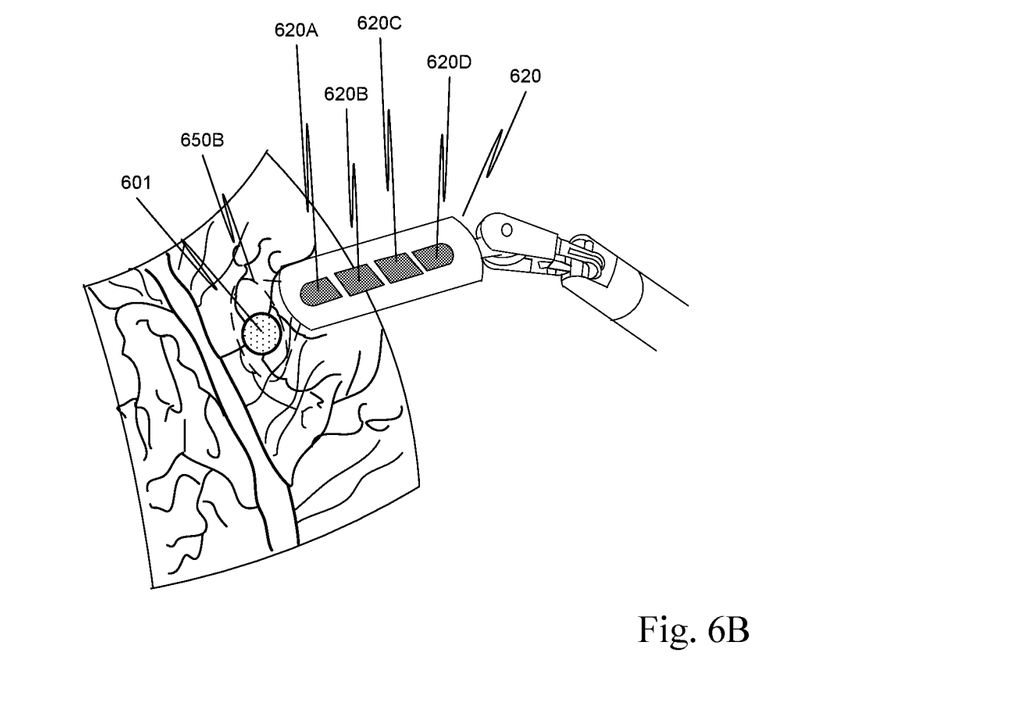

FIGS. 6A and 6B are images of a scene that includes a teleoperated radiation finder tool 620. Radiation finder tool 620 includes a plurality of stacked radiation detectors, as illustrated in FIG. 4A. In FIGS. 6A and 6B, the image of the site in the patient is truncated to help highlight the region of interest that includes a radiation site 601. In FIG. 6A, teleoperated radiation finder tool 620 is some distance away from radiation site 601, but yet some of the radiation is detected in the most distal radiation detector. Thus, the most distal visual indicator 620A is lit.

The image presented in FIG. 6A is generated using a stereoscopic camera instrument. It is know how to generate a depth map using the information captured by a stereoscopic camera instrument. See, for example, U.S. Patent Application Publication No. US 2013/0038689 A1 (disclosing "Image Capture Unit and Method with an Extended Depth of Field"), which is incorporated herein by reference. Also, a controller knows the position and orientation of the stereoscopic camera instrument in a Cartesian coordinate space and also knows the position and orientation of the teleoperated radiation finder tool 620 in that same Cartesian coordinate space. Thus, a geometric translation can be done to locate the teleoperated radiation finder tool 620 with respect to the depth map.

Next, the geometry of the radiation detectors in teleoperated radiation finder tool 620 is used to determine a cone that represents the field of view of teleoperated radiation finder tool 620, and then the controller determines the intersection of the outer surface of the cone with the tissue surface using the depth map, and generates an outline 650A of the intersection. In one aspect, the user has the option of determining the depth of the outline of the field of view. For example, the user could specify one millimeter, and outline 650A would be drawn by the controller to appear one millimeter below the surface of the tissue. This is advantageous when tissue of interest is below the surface of the tissue, because it allows the user to view the intersection of fields of view of teleoperated radiation finder tool 620 below the surface of the tissue.

In FIG. 6B, teleoperated radiation finder tool 620 has been moved to that it is closer to and over radiation site 601. Thus, all of the radiation detectors in teleoperated radiation finder tool 620 measure radiation, and so all of visual indicators 620A, 620B, 620C, and 620D are lit. This tells the user that radiation site 601 is within field of view 650B.

Hence, in one aspect, a diagnostic method for identifying tissue of interest 601 within a patient includes positioning a radiation finder tool 620, and determining the number of stacked radiation detectors in the radiation finder tool that sense radiation. See FIG. 6A. Here, tissue of interest 601 emits a radiation that is detectable by each of the stacked radiation detectors (See FIG. 4A, as an example) in radiation finder tool 620. If less than all the stacked radiation detectors detect radiation, the positioning and observing is repeated until all of the stacked radiation detectors sense radiation. The position of radiation finder tool 620 when all of the stacked radiation detectors sense radiation is such that the distal end of radiation finder tool 620 points at the tissue of interest 601, as illustrated in FIG. 6B.

Although described as a controller herein, it is to be appreciated that such a controller may be implemented in practice by any number of modules and each module may include any combination of components. Each module and each component may include hardware, software that is executed on a processor, and firmware, or any combination of the three.

Also, the functions and acts of any controller, as described herein, may be performed by one module, or divided up among different modules or even among different components of a module. When divided up among different modules or components, the modules or components may be centralized in one location or distributed across the system for distributed processing purposes. Thus, the description of a controller should not be interpreted as requiring a single physical entity as in some aspects the controller can distributed across the system.

In one aspect, a controller includes a processor that is coupled to a memory containing instructions executed by the processor. This could be accomplished within a computer system, or alternatively via a connection to another computer via modems and analog lines, or digital interfaces and a digital carrier line.

Herein, a computer program product comprises a medium configured to store computer readable code needed for any one or any combination of the methods and/or processes described herein, or in which computer readable code for any one or any for any one or any combination of the methods and/or processes described herein is stored. Some examples of computer program products are CD-ROM discs, DVD discs, flash memory, ROM cards, floppy discs, magnetic tapes, computer hard drives, servers on a network and signals transmitted over a network representing computer readable program code. A tangible computer program product comprises a medium configured to store computer readable instructions for any one or any combination of the methods and/or processes described herein, or in which computer readable instructions for any one or any combination of the methods and/or processes described herein, is stored. Tangible computer program products are CD-ROM discs, DVD discs, flash memory, ROM cards, floppy discs, magnetic tapes, computer hard drives and other physical storage mediums.

In some of the above examples, the terms "proximal" or "proximally" are used in a general way to describe an object or element which is further away from a site of interest. Similarly, the terms "distal" or "distally" are used in a general way to describe an object or element which is closer to the site of interest.

As used herein, "first," "second," "third," "fourth," etc. are adjectives used to distinguish between different components or elements. Thus, "first," "second," "third," "fourth," etc. are not intended to imply any ordering of the components or elements, or any particular number of different types of elements, e.g., three elements of the same type can be denoted as first, second, and third elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A radiation finder tool comprising:
    a body;
    a first gamma radiation detector mounted in the body;
    a collimator in the body, the collimator having a proximal end and a distal end, the proximal end of the collimator being proximal to the first gamma radiation detector; and
    a second gamma radiation detector mounted in the body, the second gamma radiation detector being configured to receive gamma radiation passed through the first gamma radiation detector and the collimator.

2. The radiation finder tool of claim 1, the body having an outer surface, the radiation finder tool further comprising:
    a first visual radiation detection indicator mounted on the outer surface of the body and coupled to the first gamma radiation detector; and
    a second visual radiation detection indicator mounted on the outer surface of the body and coupled to the second gamma radiation detector.

3. The radiation finder tool of claim 2, wherein each of the first and second visual radiation detection indicators comprises a visual indicator ring surrounding the outer surface of the body.

4. The radiation finder tool of claim 1:
    wherein the first gamma radiation detector comprises:
        a first scintillator configured to receive gamma radiation incident on the first gamma radiation detector; and
        a first photon detector coupled to the first scintillator; and
    wherein the second gamma radiation detector comprises:
        a second scintillator configured to receive radiation incident on the second gamma radiation detector; and
        a second photon detector coupled to the second scintillator.

5. The radiation finder tool of claim 4, wherein each of the first and second photon detectors comprises a solid-state photon detector array.

6. The radiation finder tool of claim 5, wherein each solid-state photon detector array comprises a single photon avalanche diode detector array.

7. The radiation finder tool of claim 4, at least one of the first scintillator and the second scintillator having a mirrored surface.

8. The radiation finder tool of claim 4, the body having a distal end, a proximal end, and a lengthwise axis extending between the proximal end and the distal end of the body;
    wherein the second scintillator has a length along the lengthwise axis that is greater than a length of the first scintillator along the lengthwise axis.

9. The radiation finder tool of claim 1, the body having a distal end, a proximal end, and a lengthwise axis extending between the proximal end and the distal end of the body, wherein:
    the first gamma radiation detector has a first area in a plane substantially perpendicular to the lengthwise axis;
    the second gamma radiation detector has a second area in a plane substantially perpendicular to the lengthwise axis;
    the second area of the second gamma radiation detector is smaller than the first area of the first gamma radiation detector.

10. A radiation finder tool comprising:
    a body having a distal end, a proximal end, and a lengthwise axis extending between the proximal end and the distal end of the body;
    a first radiation detector mounted in the body, the first radiation detector having a first area in a plane substantially perpendicular to the lengthwise axis;
    a collimator in the body, the collimator having a proximal end and a distal end, the proximal end of the collimator being proximal to the first radiation detector; and
    a second radiation detector mounted in the body, the second radiation detector being configured to receive radiation passed through the first radiation detector and the collimator, the second radiation detector having a second area in a plane substantially perpendicular to the lengthwise axis, wherein the second area of the second radiation detector is smaller than the first area of the first radiation detector.

11. The radiation finder tool of claim 10, the body having an outer surface, the radiation finder tool further comprising:
    a first visual radiation detection indicator mounted on the outer surface of the body and coupled to the first radiation detector; and
    a second visual radiation detection indicator mounted on the outer surface of the body and coupled to the second radiation detector.

12. The radiation finder tool of claim 11, wherein each of the first and second visual radiation detection indicators comprises a visual indicator ring surrounding the outer surface of the body.

13. The radiation finder tool of claim 10:
wherein the first radiation detector comprises:
- a first scintillator configured to receive radiation incident on the first radiation detector; and
- a first photon detector coupled to the first scintillator; and wherein the second radiation detector comprises:
- a second scintillator configured to receive radiation incident on the second radiation detector; and
- a second photon detector coupled to the second scintillator.

14. The radiation finder tool of claim 13, wherein each of the first and second photon detectors comprises a solid-state photon detector array.

15. The radiation finder tool of claim 14, wherein the solid-state photon detector array comprises a single photon avalanche diode detector array.

16. The radiation finder tool of claim 13, at least one of the first scintillator and the second scintillator having a mirrored surface.

17. The radiation finder tool of claim 13, wherein the second scintillator has a length along the lengthwise axis that is greater than a length of the first scintillator along the lengthwise axis.

18. A radiation finder tool comprising:
a body having an outer surface;
a first radiation detector mounted in the body;
a collimator in the body, the collimator having a proximal end and a distal end, the proximal end of the collimator being proximal to the first radiation detector;
a second radiation detector mounted in the body, the second radiation detector being configured to receive radiation passed through the first radiation detector and the collimator;
a first visual radiation detection indicator mounted on the outer surface of the body and coupled to the first radiation detector; and
a second visual radiation detection indicator mounted on the outer surface of the body and coupled to the second radiation detector.

19. The radiation finder tool of claim 18, wherein each of the first and second visual radiation detection indicators comprises a visual indicator ring surrounding the outer surface of the body.

20. The radiation finder tool of claim 18:
wherein the first radiation detector comprises:
- a first scintillator configured to receive radiation incident on the first radiation detector; and
- a first photon detector coupled to the first scintillator; and wherein the second radiation detector comprises:
- a second scintillator configured to receive radiation incident on the second radiation detector; and
- a second photon detector coupled to the second scintillator.

* * * * *

UNITED STATES PATENT AND TRADEMARK OFFICE
CERTIFICATE OF CORRECTION

PATENT NO. : 11,452,489 B2
APPLICATION NO. : 16/652509
DATED : September 27, 2022
INVENTOR(S) : Jonathan M. Sorger et al.

Page 1 of 1

It is certified that error appears in the above-identified patent and that said Letters Patent is hereby corrected as shown below:

In the Specification

At Column 1, Lines 5-8, the text:
"The present application claims priority to U.S. Provisional Patent Application No. 62/566,693, filed on October 2, 2017, and entitled "Radiation Finder Tool," the contents of which are hereby incorporated by reference in their entirety."

Should be changed to:
--The present application is a U.S. National Stage Application under 35 U.S.C. §371 of International Application No. PCT/US2018/053828, filed on October 1, 2018, and entitled "RADIATION FINDER TOOL," which claims priority to U.S. Provisional Patent Application No. 62/566,693, filed on October 2, 2017, and entitled "Radiation Finder Tool," the contents of which are hereby incorporated by reference in their entirety.--

Signed and Sealed this
Fifteenth Day of November, 2022

Katherine Kelly Vidal
*Director of the United States Patent and Trademark Office*